United States Patent
Yepez et al.

(10) Patent No.: US 9,188,577 B2
(45) Date of Patent: Nov. 17, 2015

(54) MEASURING COKING PROPENSITY

(75) Inventors: Omar Jesus Yepez, Owasso, OK (US); Ricky Eugene Snelling, Tulsa, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 92 days.

(21) Appl. No.: 13/408,626

(22) Filed: Feb. 29, 2012

(65) Prior Publication Data

US 2012/0225489 A1    Sep. 6, 2012

Related U.S. Application Data

(60) Provisional application No. 61/448,851, filed on Mar. 3, 2011.

(51) Int. Cl.
| | |
|---|---|
| *G01N 31/00* | (2006.01) |
| *G01N 33/28* | (2006.01) |
| *G01N 33/24* | (2006.01) |
| *G01V 9/00* | (2006.01) |

(52) U.S. Cl.
CPC .......... *G01N 33/2805* (2013.01); *G01N 33/241* (2013.01); *G01N 33/2835* (2013.01); *G01N 33/2888* (2013.01); *G01V 9/007* (2013.01); *Y10T 436/21* (2015.01)

(58) Field of Classification Search
CPC ............ G01N 33/241; G01N 33/2835; G01N 33/2888; G01N 33/2805; G01V 9/007
USPC .................................. 436/29, 60, 139, 6, 151
See application file for complete search history.

(56) References Cited

U.S. PATENT DOCUMENTS

| | | | | |
|---|---|---|---|---|
| 5,547,876 | A  * | 8/1996 | Chen et al. .................... | 436/159 |
| 6,294,387 | B1 | 9/2001 | Yepez et al. | |
| 6,482,311 | B1 * | 11/2002 | Wickham et al. ........ | 208/48 AA |
| 6,773,921 | B1 * | 8/2004 | Schabron et al. ............... | 436/29 |
| 2009/0117659 | A1 * | 5/2009 | Hodges ........................... | 436/60 |
| 2009/0305428 | A1 * | 12/2009 | Askins et al. .................. | 436/139 |
| 2012/0160738 | A1 * | 6/2012 | Konno et al. ................... | 208/49 |

OTHER PUBLICATIONS

The Accelerating and Retarding Effects of Hydrogen on Carbon Deposition on Metal Surfaces K.L. Yang and R.T. Yang Carbon vol. 24, No. 6, pp. 687-693.*

* cited by examiner

*Primary Examiner* — Krishnan S Menon
*Assistant Examiner* — Dwan A Gerido
(74) *Attorney, Agent, or Firm* — Phillips 66 Company

(57) ABSTRACT

The present application provides a method for measuring coking propensity of a fossil fuel, comprising mixing an iron powder with a fossil fuel, wherein the iron powder has an average particle size of less than or equal to 100 µm; reacting the iron powder with the fossil fuel at a temperature and a pressure sufficient to allow coking for a period of time; separating a supernatant and a solid product after said coking; and analyzing the solid product for carbon content, wherein the carbon content is proportional to the coking propensity. There is also provided is a method for measuring effectiveness of a coking inhibitor.

18 Claims, No Drawings

MEASURING COKING PROPENSITY

CROSS-REFERENCE TO RELATED APPLICATIONS

This application is a non-provisional application which claims the benefit of and priority to U.S. Provisional Application Ser. No. 61/448,851 filed Mar. 3, 2011, entitled "Measuring Coking Propensity," which is hereby incorporated by reference in its entirety.

FIELD OF THE INVENTION

The invention relates to measuring chemical properties of hydrocarbon fuels, more particularly to measuring coking propensity of and effectiveness of coking inhibitor additives in a hydrocarbon fuel.

BACKGROUND OF THE INVENTION

Coke is the solid carbonaceous material that can be made in many ways, including the destructive distillation of low-ash, low-sulfur bituminous coal, from cracking petroleum or from pyrolysis of biomass. Coke has many commercial uses and applications, the largest of which is as a fuel. However, it can also be undesired, fouling lines and clogging systems.

The coking behavior of a refinery hydrocarbon stream can be difficult to predict. First of all, coking is a subtle process, occurring very slowly after large amounts of hydrocarbon are exposed to heated metal. It is difficult to achieve a laboratory method to simply and accurately predict the coking reaction that will occur. Secondly, there are few good ways to rank the effectiveness of coking inhibitors. The reactions are slow, chemical amounts are low, and the affected metal surface areas are small. For example, Conradson carbon residue (CCR) measurements can indicate coking potential, but is time-consuming. Other instrumental monitoring methods for the coke lay-down reaction can also be used, but these tend to be expensive. To overcome the inherent limitations of prior techniques, either the reaction times or the sample sizes have to be large, thereby compensating for the relatively small reaction zone.

Although difficult, predicting coking behavior and inhibition are growing more important. The lighter grades of crude oil produce the best yields of fuel products, but as the world's reserves of light and medium oil are depleted, oil refineries increasingly need to process heavy oil and bitumen, using more complex and expensive methods to produce the products required. Because heavier crude oils have too much carbon and not enough hydrogen, coking is a more serious issue for heavy crude oils than it is for light crude oils. Refining generally involves removing carbon from or adding hydrogen to the molecules, and using fluid catalytic cracking to convert longer, more complex molecules to shorter, simpler ones for fuels.

U.S. Pat. No. 6,294,387 describes a method for determining corrosiveness of naphthenic acid in a fluid, including providing a fluid containing naphthenic acid; providing iron powder having a surface area of at least about 0.01 $m^2/g$; contacting the fluid and the powder for a period of time so as to provide a portion of the iron dissolved in the fluid; and measuring iron concentration of the fluid containing the dissolved iron, so to measure corrosion potential for the naphthenic acid over time. However, to our knowledge iron powder has never been used to assess coking potential before.

What is needed in the art is a one pot, simple, inexpensive and reliable method of predicting coking behavior or assessing coke inhibitors.

SUMMARY OF THE INVENTION

The present invention provides a simple and easy method of assessing the coking potential of any hydrocarbon based fuel, by reacting said fuel with very fine metal powder, such as iron powder, under typical conditions of use, and measuring the weight of the iron powder before and after said reactions. If the fuel has coked, some amount of carbon will deposit on the finely divided iron particles, thus increasing its weight. The method can also be applied to assessing the efficacy of various coking inhibitors, since the method can be applied to fuel with and without inhibitors and percent inhibition assessed.

This invention overcomes the limitations of prior methods for predicting coking behavior by directly measuring carbon accumulation of the reaction product, using a one-pot method for the coking propensity of a fossil fuel, particularly for crude oil. The large ratios of metal surface area to hydrocarbon in the method, optionally coupled with increased reaction temperatures and long exposure times, can promote coking, making the determination of coking behavior much easier to measure. The amount of carbon deposited on a metal powder, such as iron powder, after reaction with crude oil indicates coking propensity of a crude oil.

For example, iron powder and crude oil can be placed in an autoclave at temperatures of about 140° C. to about 340° C. for between about 1 hour and about 18 hours. The iron powder is separated from oil and analyzed for carbon content. When a coking inhibitor is mixed with the reaction oil, the effectiveness of additives can be measured by the reduction in coke make; that is, in a reduction of carbon content on the analyzed metal. By judiciously selecting test conditions, a map can be drawn of the coking potential under different processing scenarios.

In more detail, the present application provides a method for measuring coking propensity of a hydrocarbon fuel, comprising:

mixing a metal powder with a fluid hydrocarbon fuel, wherein the metal powder has an average particle size of less than or equal to 100 μm;

reacting the metal powder with the fluid hydrocarbon fuel at a temperature and a pressure sufficient to allow coking for a period of time;

separating the metal powder from any fluid remaining after said coking; and analyzing the metal powder for carbon content, wherein the carbon content is proportional to the coking propensity.

The metal powder can easily be separated from the hydrocarbon by filtration or centrifugation, washed with a solvent and rinsed e.g., with a volatile solvent and dried.

The carbon content can be easily determined by weighing the metal powder before and after coking and the increase in weight reflects the carbon content. Carbon content can also be measured using well-established methods in the art. Combustion Elemental Analysis can be used to determine the percent carbon on the product solid (carbon content), as well as the values of other elements such as hydrogen, nitrogen and sulfur. Carbon content can also be measured using, for example, thermal-optical reflectance (TOR) or thermo-optical transmittance (TOT) analysis.

The method can be applied to any hydrocarbon, fuel or chemical that has a tendency to coke, including fossil fuels, biomass, jet fuels, lubricating oils, etc. The method has particular applicability to crude oil and other fuels with a tendency to produce coke.

Preferably, the metal powder is any metal powder that will not otherwise interfere with the fuel use and allows deposition of coke onto its surface. Iron powder may be preferred as inexpensive and readily available. Preferably, the powder has an average particle size of ≤100 μm, and preferably is even finer. Thus, the powder can have an average particle size, for example, from 1 μm to 50 μm, or from 1 μm to 10 μm. In some cases, the powder can be even finer, about 0.1 μm, however, there may be a lower limit on size because it should still be easy and efficient to separate the solid powder from the fluid after the coking is complete.

The temperature, pressure and length of the reaction should be about the same conditions at which a particular fuel is used, and in many cases that will be sufficient to produce some amount of coking Generally, the temperature is from 100° C. to 400° C., 140° C. to 350° C., or 300° C. to 340° C. The pressure can be from 1 kPa to 650 kPa, or 10 kPa to 400 kPa. The period of time can be from 1 hour to 18 hours, for example from 2 hours to 15 hours. If desired, the temperature and/or pressure can be increased to speed up the reaction, and then corrected for in determining coking at a particular temperature.

The present application also provides a method for measuring effectiveness of a coking inhibitor, comprising:

mixing a metal powder with a fluid hydrocarbon fuel and a coking inhibitor, wherein the metal powder has an average particle size less than 100 μm;

treating the metal powder with the hydrocarbon fuel and coking inhibitor at a temperature and a pressure for a period of time sufficient to allow coking;

separating said metal powder and any remaining fluid after said treating step;

analyzing the solid product for a first carbon content x;

obtaining a second carbon content y for the hydrocarbon fuel without coking inhibitor;

calculating percent inhibition of the coking inhibitor using the following equation: 100−100x/y=percent inhibition. The step of obtaining a second carbon content y can be essentially the same steps, only performed without the coking inhibitor. It is also possible to conduct the tests over a range of temperatures and/or pressures, and thus obtains curves of coking behavior.

DESCRIPTION OF EMBODIMENTS OF THE INVENTION

The following abbreviations are used herein:

| | |
|---|---|
| API | American Petroleum Institute |
| CCR | Conradson carbon residue |
| PAH | Polycyclic aromatic hydrocarbons |
| PSD | Particle size distribution |
| TOR | Thermal-optical reflectance |
| TOT | Thermal-optical transmittance |

"Biomass" refers to any biological material from living, or recently living organisms, such as wood, paper, agricultural waste, consumer waste, wood and paper waste, cereal and grass crops, vegetable and tree oils, algae, and the like.

"Biomass fuel" or "biofuel" refers to a fuel derived from biological material of living or recently living organisms. Examples of biomass fuel include wood, charcoal, hydrogen gas, alcohol (e.g., ethanol), organic oils (e.g., palm oil, rapeseed, jathorpa), manure, grass cuttings, and biodiesel. Sources of biological materials used in biomass fuel include, but are not limited to trees (e.g., poplar, pine, willow, oak, maple, eucalyptus, oil palm), miscanthus, switchgrass, hemp, corn, cassava, sorghum, sugarcane, sugar beet, soybean, sunflower, wheat, rapeseed, jathorpa, salicornia, mahua, mustard, flax, field pennycress, *pongamia pinnata*, agricultural waste and algae.

"Bitumen" or "asphalt" refers to a mixture of organic liquids that is highly viscous, black, sticky, entirely soluble in carbon disulfide, and composed primarily of highly condensed polycyclic aromatic hydrocarbons (PAHs). Naturally occurring, crude bitumen is a tar-like form of petroleum so thick and dense that it must be heated or diluted before it can flow. Refined bitumen is the residual (bottom) fraction obtained by fractional distillation of crude oil.

"Crude oil" refers to a type of fossil fuel in the form of a mineral oil consisting of a mixture of hydrocarbons of natural origin, yellow to black in color, of variable specific gravity and viscosity. Crude oil is often referred to simply as "crude" or generally as "petroleum". Crude oil is typically its geography of origin, American Petroleum Institute (API) gravity, and sulfur content. Crude oil is "light" if it has low density or "heavy" if it has high density; "sweet" if it contains relatively little sulfur or "sour" if it contains substantial amounts of sulfur. Light crude oil is more desirable than heavy oil because it produces a higher yield of gasoline. Sweet crude oil commands a higher price than sour crude oil because it has fewer environmental problems and requires less refining to meet sulfur standards imposed on fuels in consuming countries. Each crude oil its own molecular characteristics. See Table 1 for examples of crude oil.

TABLE 1

Examples of crude oil

| Name | API gravity | Sulfur content (% mass) | Location of field |
|---|---|---|---|
| Arab Extra Light | 39.4° | 1.09% | Saudi Arabia |
| Arab Heavy | 27.7° | 2.87% | Saudi Arabia |
| Arab Light | 32.8° | 1.97% | Saudi Arabia |
| Arab Medium | 30.2° | 2.59% | Saudi Arabia |
| Brent Blend | 38.3° | 0.37% | United Kingdom |
| Dubai | 31° | 2.0% | Dubai |
| Merey | | | Venezuela |
| West Texas Intermediate (WTI) | 39.6° | 0.24% | United States |
| West Texas Sour (WTS) | 31.7° | 1.28% | United States |

"Coke" refers to solid carbonaceous material derived from hydrocarbon fuels. Coal, for example, produces coke from destructive distillation of low-ash, low-sulfur bituminous coal. Coke derived from petroleum is referred to as "petroleum coke" or "pet coke" or "petcoke", for example carbonaceous solid derived from oil refinery coker units or other cracking processes, or hard carbon and other crude oil impurities formed on the inside furnace tubes. Coke has several industrial uses, including, but not limited to, making electrodes for aluminum manufacturing, fuel, and steel manufacture.

"Coking" refers to a process of forming coke from a hydrocarbon-containing starting material. For example, a starting material can be heated from about 100° C. to about 450° C., wherein lower molecular weight chemicals are distilled off and coke is left behind. Coking can be used to improve hydrocarbon liquids for further upgrading by catalytic processing because many chemicals that poison catalysts have been removed. Removal of heteroatoms from the starting material is counterbalanced by increased hydrogen content in the supernatant, because most polynuclear aromatic building blocks in the petroleum contain heteroatoms that reactively separate into the coke.

"Coking inhibitor" refers to a chemical that reduces the rate of coke formation. Examples of coking inhibitors include, but are not limited to, benzothiazole, hydrogen, hydrogen sulfide, phosphonates, thiophosphonates, phosphoric triamides, and thiophene.

"Conradson carbon" or "Conradson carbon residue (CCR)" refers to an industrial coking test for characterizing the coke-forming tendency of petroleum liquids. Though widely used in the petroleum industry, CCR is time-consuming, requiring complete evaporation and pyrolysis of the fossil fuel under analysis. CCR is linear with respect to hydrogen content, as can be independently verified by directly measuring the hydrogen content of the coke in the microcarbon test and converting independent hydrogen content of distillable supernatant. CCR is conserved for physical separations (hydrogen is conserved), increases for thermal conversion (hydrogen escapes as part of hydrocarbon gas byproduct), and decreases for hydroconversion (hydrogen is added).

"Hydrocarbon fuel" refers to any fuel, including fossil fuels, biomass fuels, and the like. "Fossil fuel" refers to fuel formed from natural resources, such as anaerobic decomposition of organisms, for example phytoplankton, zooplankton, and plant matter. Fossil fuels can include coal, crude oil, and natural gas.

"Metal powder" refers to a metal or alloy in powdered, pulverized, comminuted, or particulate form. The metal can be a transition metal, such as Sc, Ti, V, Cr, Mn, Fe, Co, Ni, Cu, Zn, Y, Zr, Nb, Mo, Ru, Rh, Pd, Ag, La, Hf, Ta, W, Re, Ir, Pt, and Au, or a rare earth metal, such as Ce, Pr, Nd, Pm, Sm, Eu, Gd, Tb, Dy, Ho, Er, Tm, Yb, or Lu. An alloy is a partial or complete solid solution of one or more elements in a metallic matrix. Suitable alloys include, but are not limited to, steel, cast iron, bronze, brass, cast copper, cast aluminum, and nitinol. In particular, the alloy can be a steel alloy with various trace metal content. Use of such steel alloys would allow determination and selection of a steel with diminished coking potential. In some embodiments, the metal powder is iron powder.

"Iron powder" refers to material consisting essentially of elemental iron (Fe0) in powdered, pulverized, comminuted, or particulate form. Iron powder can have an average particle size from about 100 µm to about 0.1 µm, such as from about 50 µm to about 1 µm, for example from about 10 µm to about 5 µm, from about 50 µm to about 5 µm, or from about 10 µm to about 1 µm. Most preferably, the iron powder has an average particle size of about 6 µm. Particles sizes can also be described using a mesh scale, wherein a 400 mesh powder has an average particle size of about 38 µm, 500 mesh of about 25 µm, 635 mesh of about 20 µm, 1200 mesh of about 12 µm, and 2400 mesh of about 6 µm.

"Average particle size" or "average equivalent diameter" refers to the diameter where 50 mass % of particles in a powder have a larger equivalent diameter, and the other 50 mass % have a smaller equivalent diameter. For example, average particle size can be denoted as equivalent D50, which can be read from a cumulative particle size distribution (PSD) graph. From the point where the 50% horizontal line intersects the PSD curve, a line can be drawn perpendicular to the x-axis. The numerical value of D50 can be interpolated from the intersection of the perpendicular with the x-axis. D10 refers to an equivalent diameter where 10 mass % of the particles in a powder have a smaller diameter, hence the remaining 90 mass % are coarser (i.e., have a larger diameter). D90 refers to an equivalent diameter where 90 mass % of particles in a powder have a smaller diameter and only 10 mass % are coarser.

The surface area of a powder is inversely proportional to the particle size of that powder. That is, the smaller that the particles are in the powder, the larger the surface area of that powder. Conversely, the larger that the particles are in the powder, the smaller the surface area of that powder. A high surface area material has a high surface area to volume ratio, which can typically be about greater than about 200 m2/g, such as from 300 m2/g to about 2000 m2/g. High surface area is desirable as it drives the reaction.

In some embodiments, a high surface area metal powder and a test crude oil are placed in a batch reactor under temperatures of about 100° C. to about 450° C., such as about 140° C. to about 400° C., for example 260° C. to about 340° C. Coking can occur at pressures of, for example, about 1 kPa, about 5 kPa, about 10 kPa, about 20 kPa, about 30 kPa, about 100 kPa, or about 200 kPa, about 400 kPa, or about 650 kPa. The reaction mixture is stirred for about 1 hour to about 72 hours, such as for about 2 hours to about 48 hours, for example about 5 hours to about 18 hours. Standard test conditions can also be set by a standards body, thus making the test directly comparable across industries or uses.

Once the coking reaction is sufficiently complete, the fluid (or supernatant) remaining after coking is filtered and the resulting solids are analyzed for carbon. For example, the difference in weight between the iron powder and the solid product is the amount of new carbon content that resulted in coking from the fossil fuel. The carbon content can also be determined using other methods established in the art, including, thermal-optical analysis.

In thermal-optical analysis, organic compounds can be volatilized from the sample in a helium atmosphere at lower temperatures than elemental carbon can be oxidized or removed. The analyzer liberates carbon compounds under different temperature and oxidation environments from a sample; converts these compounds to carbon dioxide by passing the volatilized compounds through an oxidizer, for example heated manganese dioxide (MnO2); reduces CO2 to methane by passing the flow through a methanator, for example hydrogen-enriched nickel catalyst; and quantifies methanol equivalents using a detector, for example a flame ionization detector (FID).

The principal function of the optical component, typically a laser reflectance or laser absorption device, is to correct for pyrolysis of organic carbon compounds to elemental carbon. Without this correction, the organic carbon fraction is underestimated and the elemental carbon fraction is overestimated, because some pyrolyzed organic carbon is included. Filter reflectance (or transmittance) is continuously monitored throughout an analysis cycle, for example, using a helium-neon laser and a photodetector throughout an analysis cycle. Reflectance, largely dominated by the presence of light-absorbing elemental carbon, decreases as pyrolysis occurs and increases as light-absorbing carbon is liberated during the latter part of the analysis. By monitoring the reflectance or transmittance, the portion of the elemental carbon peak corresponding to pyrolyzed organic carbon can be accurately assigned to the organic fraction.

The present invention is exemplified with respect to a novel method for measuring coking propensity of a hydrocarbon fuel and effectiveness of a coking inhibitor. However, this method is exemplary only, and the invention can be broadly applied to, for example, measurements of carbon content. The following examples are intended to be illustrative only, and not unduly limit the scope of the appended claims.

EXAMPLE 1

Iron powder with an average particle size of about 6 µm was placed into a batch reactor with a test crude oil. The mixture was stirred for about 1 hour to about 18 hours at temperatures from about 140° C. to about 340° C. and at a pressure where coking typically does occur. The pressure can be 0 pounds per square inch (psig) to 500 psig (3.44 MPa), for example, 100 psig to 400 psig (0.689 MPa to 2.76 MPa), or 150 to 250 psig (1.03 MPa to 1.72 MPa). In a particular, a pressure of 200 psig (1.38 MPa) can be used. Hydrogen is present in system gases, so increased pressure of the system gas necessarily increases hydrogen pressure which, in turn, can inhibit coking Hydrogen pressure can also be used to test coking propensity in the lab under conditions found in the field.

After a designated time passed, supernatant was filtered and the resulting solids were analyzed for carbon content. Tables 2-5 provide the data from tests on four crude oils. Fresh iron powder contained 0.65% carbon before the experiment, as assessed by combustion elemental analysis on Perkin Elmer 2400 Series II CHNS/O Elemental Analyzer. Values obtained after coking were thus corrected by subtraction of 0.65. Table 6 contains a summary of the corrected data at 300° C. and at 340° C.

TABLE 2

Post Run Solids Carbon Content Data from Oklahoma Sour (OKS) crude oil

| Temperature | % C | corrected % C |
|---|---|---|
| 140° C. | 0.90 | 0.25 |
| 180° C. | 0.86 | 0.21 |
| 220° C. | 0.75 | 0.10 |
| 260° C. | 0.80 | 0.15 |
| 300° C. | 0.79 | 0.14 |
| 340° C. | 1.65 | 1.00 |

TABLE 3

Post Run Solids Carbon Content Data from Peck crude oil

| Temperature | % C | corrected % C |
|---|---|---|
| 140° C. | 0.75 | 0.10 |
| 180° C. | 0.86 | 0.21 |
| 220° C. | 0.76 | 0.11 |
| 260° C. | 0.80 | 0.15 |
| 300° C. | 0.80 | 0.15 |
| 340° C. | 1.00 | 0.35 |

TABLE 4

Post Run Solids Carbon Content Data for Western Texas Sour (WTS)

| Temperature | % C | corrected % C |
|---|---|---|
| 140° C. | 3.04 | 2.39 |
| 180° C. | 2.26 | 1.61 |
| 220° C. | 1.74 | 1.09 |
| 260° C. | 1.37 | 0.72 |
| 300° C. | 1.09 | 0.44 |

TABLE 5

Post Run Solids Carbon Content Data for Merey crude oil

| Temperature | % C | corrected % C |
|---|---|---|
| 140° C. | 1.15 | 0.50 |
| 180° C. | 1.00 | 0.35 |
| 220° C. | 0.83 | 0.18 |
| 260° C. | 0.96 | 0.31 |
| 300° C. | 0.38 | 0.18 |

TABLE 6

Corrected % Carbon

| Crude Oil Product | @ 300° C. | @ 340° C. |
|---|---|---|
| Merey | 0.18 | |
| OKS | 0.14 | 1.00 |
| WTS | 0.44 | |
| Peck | 0.15 | 0.35 |

The experimental results show that at 300° C., the four crudes have different amounts of coke deposited on the filtered post-reaction solids. This difference is a measure of the tested materials' potential to form coke. The difference is starker at 340° C., as can be seen in the difference between OKS and Peck crudes. At 300° C., the difference between corrected % C was only 0.01, but at 340° C., the difference was 0.65. Also, at 300° C., WTS produced roughly 2-3 times the amount of coke as the other samples of crude. At 340° C., the amount of coke overwhelmed the scoping test.

In conclusion, this test told us the temperature dependence of coking propensity. At a temperature of 300° C., Oklahoma Sour (OKS) and Peck crudes had similar coking propensities. But at higher temperatures, in this example 340° C., the Oklahoma Sour crude produced three times as much coke as Peck crude in this lab test.

Longer reaction times and high surface area of the iron powder favors coke formation. Carbon accumulation is a direct measure of a crude oil's coking propensity, providing significant advantages in time, cost savings and efficiency over prior indirect coking measurements, such as the Conradson carbon residue test. Further, these iron powder experiments are an effective way to evaluate and rank coking inhibitor additives.

The following reference is incorporated by reference in its entirety: U.S. Pat. No. 6,294,387.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

What is claimed is:

1. A method for measuring coking propensity of a hydrocarbon fuel comprising crude oil, comprising:
   a) mixing a metal powder with the fluid hydrocarbon fuel, wherein the metal powder has an average particle size of less than or equal to 100 µm;

b) reacting the metal powder with the fluid hydrocarbon fuel at a temperature and a pressure sufficient to allow coking for a period of time wherein the pressure is at least 1 MPa and less than 3 MPa and the period of time is at least five hours;

c) separating said metal powder from any remaining fluid after said coking; and d) analyzing the metal powder for carbon content, wherein the carbon content is proportional to the coking propensity and wherein the analysis includes thermal-optical analysis to correct for organic carbon included in the measured carbon content.

2. The method of claim 1 wherein the carbon content is determined by instrumental combustion analysis.

3. The method of claim 1 wherein the carbon content is determined by weighing the metal powder before and after coking and the increase in weight is the carbon content.

4. The method of claim 1 wherein the metal powder is iron powder.

5. The method of claim 1, wherein the pressure is from 1 MPa to 2 MPa.

6. The method of claim 1, wherein the metal powder has an average particle size from 50 μm to 1 μm.

7. The method of claim 6, wherein the metal powder has an average particle size from 10 μm to 1 μm.

8. The method of claim 1, wherein the temperature is from 100° C. to 400° C.

9. The method of claim 8, wherein the temperature is from 300° C. to 340° C.

10. The method of claim 1, wherein the period of time is up to 72 hours.

11. The method claim 10, wherein the period of time is from 5 hours to 18 hours.

12. A method for measuring coking propensity of a crude oil, comprising:

a) mixing an iron powder with a crude oil, wherein the iron powder has an average particle size of less than or equal to 100 μm;

b) reacting the iron powder with the crude oil at a temperature and a pressure for a period of time sufficient to allow coking wherein the pressure is at least 1 MPa and less than 3 MPa and the period of time is at least five hours, c) separating said metal powder from any remaining fluid after said coking; and d) analyzing the solid product for carbon content wherein the analysis includes thermal-optical analysis to correct for organic carbon included in the measured carbon content, and wherein the carbon content is proportional to the coking propensity of said crude oil.

13. The method of claim 12, wherein the temperature is from 100° C. to 400° C.

14. A method for measuring effectiveness of a coking inhibitor for a fluid hydrocarbon comprising crude oil, comprising:

a) mixing a metal powder with the fluid hydrocarbon and a coking inhibitor, wherein the metal powder has an average particle size less than 100 μm;

b) reacting the metal powder with the fluid hydrocarbon and coking inhibitor at a temperature and a pressure for a period of time sufficient to allow coking wherein the pressure is at least 1 MPa and less than 3 MPa and the period of time is at least five hours;

c) separating said metal powder and any remaining fluid after said coking;

d) analyzing said metal powder for a first carbon content x wherein the analysis includes thermal-optical analysis to correct for organic carbon included in the first carbon content;

e) obtaining a second carbon content y for the fluid hydrocarbon without coking inhibitor wherein thermal-optical analysis is used to correct for organic carbon included in the second carbon content;

f) calculating percent inhibition of the coking inhibitor using the following equation: $100-100x/y=$percent inhibition.

15. The method of claim 14, wherein obtaining a second carbon content y, comprises a) mixing a second sample of the metal powder with a second sample of the fluid hydrocarbon without coking inhibitor;

b) reacting the second sample of iron powder with the second sample of the fluid hydrocarbon at the same temperature, pressure and period of time as for obtaining the first carbon content x;

c) separating said second sample of the metal powder and any remaining second sample of fluid hydrocarbon after coking; and d) analyzing the second sample of metal powder for a second carbon content y.

16. The method of claim 14, wherein the temperature is from 300° C. to 340° C.

17. The method of claim 14 wherein the carbon content is determined by instrumental elemental analysis.

18. The method of claim 14 wherein the metal powder is iron powder.

* * * * *